US006365622B1

(12) United States Patent
Cavazza

(10) Patent No.: US 6,365,622 B1
(45) Date of Patent: Apr. 2, 2002

(54) ANTIOXIDANT COMPOSITION COMPRISING ACETYL L-CARNITINE AND α-LIPOIC ACID

(75) Inventor: Claudio Cavazza, Rome (IT)

(73) Assignee: Sigma-Tau HealthScience S.p.A., Rome (IT)

( * ) Notice: Subject to any disclaimer, the term of this patent is extended or adjusted under 35 U.S.C. 154(b) by 0 days.

(21) Appl. No.: 09/786,153

(22) PCT Filed: Aug. 19, 1999

(86) PCT No.: PCT/IT99/00268

§ 371 Date: Mar. 12, 2001

§ 102(e) Date: Mar. 12, 2001

(87) PCT Pub. No.: WO00/11968

PCT Pub. Date: Mar. 9, 2000

(30) Foreign Application Priority Data

Sep. 1, 1998 (IT) .................................. RM98A0566

(51) Int. Cl.⁷ .................... A61K 31/385; A61K 31/205
(52) U.S. Cl. ........................................ 514/440; 514/556
(58) Field of Search ................................. 514/440, 556

(56) References Cited

U.S. PATENT DOCUMENTS

| 5,916,912 A | 6/1999 | Ames et al. |
| 5,977,162 A | 11/1999 | Seidman |

FOREIGN PATENT DOCUMENTS

| EP | 0 797 993 | 10/1997 |
| WO | WO95/01096 | 1/1995 |
| WO | WO97/02041 | 1/1997 |
| WO | WO98/3494 | 8/1998 |
| WO | WO98/41113 | 9/1998 |

OTHER PUBLICATIONS

Ames, B.: "Micronutrients prevent cancer and delay aging" Toxicology Letters, vol. 102, Dec. 1998, pp. 5–18.

*Primary Examiner*—Raymond Henley, III
(74) *Attorney, Agent, or Firm*—Nixon & Vanderhye

(57) ABSTRACT

A composition containing the active ingredients acetyl L-carnitine and α-lipoic acid for the prevention and/or therapeutic treatment of various alterations and pathological states induced by free radicals, that may be in the form of a dietary supplement, dietetic support or of an actual medicine.

15 Claims, No Drawings

ANTIOXIDANT COMPOSITION COMPRISING ACETYL L-CARNITINE AND α-LIPOIC ACID

This is A 371 of PCT/IT99/00268 filed Aug. 19, 1999.

The present invention relates to a composition for the prevention and/or treatment of tissular diseases brought about by the presence of free radicals due to environmental pollution; brain or myocardial damages induced by free radicals following cerebral or myocardial ischaemia and attendant riperfusion; of the toxic or diabetic neuropathies and of metabolic disorders in the glucose utilization.

Accordingly, the composition may take the form and exert the action of a dietary supplement or of an actual medicine, depending upon the support or preventive action, or the strictly therapeutic action, which the composition is intended to exert in relation to the particular individuals it is to be used in.

More particularly the present invention relates to an orally, parenterally, rectally or transdermally administrable composition which comprises in combination:

(a) acetyl L-carnitine or a pharmacologically acceptable salt thereof, optionally in combination with at least another "carnitine" where for "carnitine" is intended L-carnitine or an alkanoyl L-carnitine selected from the group comprising propionyl L-carnitine, valeryl L-carnitine, isovaleryl L-carnitine or their pharmacologically acceptable salts; and (1) α-lipoic acid.

A systemic deficiency of alkanoyl L-carnitines (ubiquitous naturally-occurring compounds, the greatest concentrations of which are to be found above all in skeletal muscle and in the myocardium) is known to lead to muscular and functional deficits which can be restored to normal by the exogenous administration of these compounds.

The presence of acetyl L-carnitine has been ascertained both at cerebral level and in peripheral nervous tissue where its presence is necessary for normal nerve conduction.

The production of energy by carnitines occurs via intra-mitochondrial β-oxidation of fatty acids, as well as via the oxidation of branched-chain amino acids and regulation of insulin activity.

Important for the purposes of the characterization of the biological activity of carnitines are studies indicating their stabilising effects on cellular phospholipid membranes and on the integrity and deformability of erythrocytes.

Acetyl L-carnitine in particular protects cerebral tissue against peroxidative phenomena. While it has been ascertained that carnitine is necessary for normal growth, it is equally true that reduced carnitine levels compared to normal have been detected during ageing.

During the metabolic processes associated with ageing, an increase in oxidative processes is constantly detected together with a related increase in free radicals, which facilitates the onset of diabetic lesions.

Reduced mitochondrial activity leads to an increase in oxidants which the cell defences are no longer able to combat effectively.

The increase in peroxides, hydroxides and singlet oxygen produced by aerobic metabolism may lead to damage to macromolecules (DNA, proteins and lipids), which contributes to the onset of degenerative diseases, including diabetes, which usually arise during ageing. The reduced mitochondrial activity which comes about with ageing is also accompanied by a reduction in cardiolipin, a diphosphatyl-glycerol derivative which makes up part of the structure of the mitochondrial membrane and plays an important role in maintaining mitochondrial activity, particularly at the level of fatty acid β-oxidation processes. Mitochondrial activity, including the fatty acid β-oxidation processes, can be reactivated by the administration of acetyl L-carnitine, which is also capable of restoring normal cardiolipin concentrations in the mitochondria.

The positive effect of acetyl L-carnitine on mitochondrial activity is also proved by its ability to promote the utilization of the glycolytic pathway for ATP production. These effects are detected particularly at the neuronal level where acetyl L-carnitine has proved capable of preventing neuronal lesions or chronic neuronal degeneration.

In addition to a reduction in the carnitines present in the body during the processes of ageing, a reduction in growth factors (GF-I) is also detected and particularly a reduction in IGF-I (insulin-like growth factor).

IGF-I, IGF-II and relaxin are peptides belonging to the group of proinsulins also called somatomedins.

IGFs exert a homeostatic and trophic action, particularly at both central and peripheral nervous system level, and the clinical use of these peptides has yielded beneficial results in many degenerative nervous disorders including diabetic neuropathy.

The correlations existing between ageing and a reduction in carnitines and growth factors, including IGF-I, and the restoration of the levels of these factors by means of the exogenous administration of acetyl L-carnitine justify the interest in carnitines for the purposes of their use in the prevention and treatment of neurodegenerative diseases, including diabetic neuropathy.

It has been demonstrated that α-lipoic acid also performs an important regulatory function on carbohydrate metabolism and insulin activity. α-lipoic acid is widely distributed in nature in both the vegetable and animal worlds and can be taken with food. Recognised first as a growth factor for a number of micro-organisms, it was then isolated in ox liver as bound to many animal proteins. It acts as an important scavenger of free radicals, above all those deriving from environmental contamination. Recently, it has been shown that this compound is also useful in the regulation of glucose utilization and of insulin activity, so much so as to constitute an important factor in the prevention of diabetic neuropathies.

It has been demonstrated that lipid peroxidation, which is increased in diabetic neuropathy, can be controlled and reduced, both at cerebral level and at the level of the sciatic nerve or the ocular lens, by the administration of α-lipoic acid or one of its enantiomers. Moreover, α-lipoic acid inhibits the aldose reductase activated by hyperglycaemia, and therefore α-lipoic acid may also play an important therapeutic role in diabetic complications.

α-lipoic acid enhances the insulin-induced muscular utilisation of glucose and, in diabetic subjects, reduces resistance to the effects of insulin on glucose. Related to the antioxidant effect of α-lipoic acid are also its neuro-protective capability against brain damage induced by ischaemia and its postulated therapeutic role in Parkinson's disease and AIDS.

The antioxidant effect of α-lipoic acid may be either direct or indirect, via restoration of glutathione and ascorbic acid concentrations.

While the action of α-lipoic acid on carbohydrate metabolism is due essentially to its ability to act as a coenzyme in the oxidative decarbohydroxylation of pyruvate and other α-ketoacids and, through the acetates, in the activation of the tricarboxylic acid cycle leading to the formation of ATP, for the purposes of explaining the multiple favourable biological effects that this compound has in preventing diabetic damage, other pathways whereby α-lipoic acid exerts its protective action should also be borne in mind.

Among these, one should bear in mind particularly the mechanism consisting in its ability, after reduction to dihydrolipoic acid, to inhibit the activation of the nuclear transcription factor (NF-kB) by reactive oxygen species (ROS), thus, in turn, inhibiting the associated cascade of neurotoxic and cytotoxic factors.

Since many of the complications associated with diabetes, such as neuropathies and ocular cataracts are mediated by ROS, inhibition of activation of the nuclear transcription factor may constitute a mechanism via which α-lipoic acid may intervene in the prevention of diseases related to diabetes. Furthermore, one should also bear in mind that, in diabetic subjects, the concentrations of α-lipoic acid are lower than normal values and that the administration of α-lipoic acid may restore these levels to normal. It thus has an additive effect to that of insulin in glucose transport to the cell membranes.

Chronic exposure to high concentrations of glucose may lead to a non-enzymatic reaction between glucose and proteins and to the spontaneous formation of highly reactive proteins known as end products of glycosylation (Advanced Glycosylation End Products=AGEs). Among these, the gylcosylation products of glucose and albumin, glucose and collagen, and glucose and haemoglobin are those most studied. The effects that AGEs give rise to in tissues and cells are all relevant factors in explaining a large proportion of diabetic diseases at nervous, muscular and endothelial level.

AGEs, in fact, enhance the synthesis of the components of the extracellular matrix, increase endothelial permeability and the formation of immune complexes and cytokines, and cause neuronal and retinal ischaemia, myelin accumulation and myelinic degeneration. A number of these compounds are formed both in the course of diabetes and during ageing.

A correlation between AGEs and activation of NF-IKB has recently been demonstrated, as has the ability of x-lipoic acid to inhibit this reaction.

Protein glycation and glucose oxidation by glucose at high concentrations together with free radicals may, therefore, be another of the causes responsible for the tissue abnormalities—particularly nerve tissue abnormalities—associated with diabetes. The presence of α-lipoic acid also inhibits or limits the progression of glycosylation or glucose oxidation reactions.

Another protective effect of α-lipoic acid has also been observed in pancreatic cells placed in contact with inflammatory agents.

As regards the action of α-lipoic acid in the prevention and cure of cataracts, this may be attributable not only to the other mechanisms described above, but also to restoration of vitamin C concentrations in the eye which are reduced by hyperglycaemia due to competition of glucose with vitamin C transport.

In addition to a sparing of vitamin E and an increase in glutathione concentrations, the protective action of α-lipoic acid against the onset of neuropathies has also been confirmed by clinical studies. It has been observed that the reduction in nervous lesions is also accompanied by a reduction in peroxidative reaction products as detected by the lowering of malonylaldehyde concentrations. Other multicentre studies have confirmed its activity in the treatment of diabetic neuropathies.

Surprisingly it has been found that a composition comprising as its characterising components a combination of:

(a) acetyl L-carnitine or a pharmacologically acceptable salts thereof, and
(b) α-lipoic acid is extremely effective in the prevention and/or treatment of tissue damage induced by the presence of free radicals due to environmental pollution; of cerebral or myocardial lesions induced by free radicals after cerebral or myocardial ischaemia and as a result of reperfusion; of toxic or diabetic neuropathies, and of metabolic disorders in the glucose utilization.

It has also been found that, advantageously, component (a) may further comprise a "carnitine" selected from the group comprising L-carnitine, propionyl L-carnitine, valeryl L-carnitine and isovaleryl L-carnitine or their pharmacologically acceptable salts thereof, The (a):(b) weight-to-weight ratio ranges from 100:1 to 1:10.

Toxicological Tests

Both carnitines and α-lipoic acid are well known for their very limited toxicity and good tolerability. These favourable toxicological characteristics of carnitines and α-lipoic acid have been confirmed by combining these components and administering them at high doses both to rats and mice. In these animals, in fact, it proved possible to administer amounts of up to more than 250 mg/kg of acetyl L-carnitine or 100 mg/kg of α-lipoic acid parenterally, as well as of 250 mg/kg of a mixture of carnitines (acetyl L-carnitine, propionyl L-carnitine, isovaleryl L-carnitine combined in a 1:1 weight ratio to one another) and more than 500 mg/kg of acetyl L-carnitine, 500 mg/kg of the carnitine mixture and 200 mg/kg of α-lipoic acid orally without any of the animals thus treated dying.

Also prolonged administration via the diet for 30 consecutive days, both in a group of rats and in a group of mice, of 200 mg/kg of acetyl L-carnitine or 200 mg/kg of the carnitine mixture together with 100 mg/kg of α-lipoic acid proved to be well tolerated and led to the detection of no signs of toxicity. Both the weight gain and the various blood-chemistry tests performed in these animals showed normal values, as did the findings of histopathology tests performed on the main organs after sacrificing the animals at the end of treatment.

Neuroprotective Activity Tests in Experimental Cerebral Ischaemia

In view of the fact that lesions due to cerebral ischaemia are related to the production of free radicals and of nitrous oxide and that both carnitines and α-lipoic acid afford protection against the toxic action of free radicals, in these tests cerebral ischaemia was induced by occluding the middle cerebral artery (MCA) according to the method described by Scharkey (Scharkey, Y., Nature 371–336, 1994) by injecting endothelin-1 (120 pmol in 3 nl) into the anaesthetised rat in three minutes with a microcannula placed stereotactically in the piriform cortex at the level of the middle cerebral artery. Occlusion of the artery is induced, and the resulting ischaemia can be checked three days after this procedure by transcardiac perfusion of a solution of paraformaldehyde (4% in PBS).

After removing the brain, it was placed in fixative containing 10% sucrose, and cryostatic sections (20 nm) fixed with cresyl violet were examined under the optical microscope. Acetyl L-carnitine (50 mg/kg), or the carnitine mixture (50 mg/kg of a mixture of acetyl L-carnitine, propionyl L-carnitine, and isovaleryl L-carnitine in a 1:1 weight ratio to one another), or α-lipoic acid (20 mg/kg) were administered intravenously 5 minutes after the endothelin injection.

The volume of the infarcted area was calculated according to the method described by Park (Park C. K., *Anns. Neurol.*, 20–150, 1989). The results of these tests demonstrate that acetyl L-carnitine, the carnitine mixture, and α-lipoic acid are all capable of reducing the ischaemic area, but, surprisingly, the greatest and most significant result can be obtained with a combination of these products and, in particular, with a combination of acetyl L-carnitine and α-lipoic acid.

TABLE 1

Extent of ischaemia (volume in mm³) due to occlusion of the MCA (percentage reduction of volume compared to controls)

|  | Volume (mm³) |
| --- | --- |
| Acetyl L-carnitine | 25.6 ± 1.5 |
| α-Lipoic acid | 34.5 ± 2.1 |
| Carnitine mixture | 35.8 ± 3.1 |
| Acetyl L-carnitine + α-lipoic acid | 85.3 ± 4.4 |
| Carnitine mixture + α-lipoic acid | 80.5 ± 6.1 |

Experimental Diabetic Hyperglycaemia Tests

Hyperglycaemia, whether through the formation of protein glycosylation products (AGEs) or through metabolic hypoxia, is one of the underlying factors responsible for diabetic disease and particularly for diabetic neuropathy.

Controlling serum glucose is therefore one of the most important means of preventing diseases related to diabetes. In these tests, experimental diabetes was induced in rats, and tests were then performed to establish whether the induced hyperglycaemia could be reduced by the administration of acetyl L-carnitine, or carnitine mixture, or α-lipoic acid, or combinations of these products. The hyperglycaemia was induced by subcutaneous injection of alloxan (100 mg/kg) in the rat, and those rats were considered hyperglycaemia which presented serum glucose levels above 450 mg/dl seven days after the alloxan injection.

Treatment with the test substances was given orally for a period of three weeks. At the end of this period, serum glucose was measured in the various groups of rats, both hyperglycaemic and treated.

The results obtained demonstrate that both carnitines and α-lipoic acid alone are capable of only slightly lowering the high initial serum glucose values, but the most significant result is that which appears after administration of carnitines in admixture with α-lipoic acid. In this case, particularly with the combination of acetyl L-carnitine and α-lipoic acid, there is a marked synergistic action of the two products which are capable of bringing serum glucose values down almost to normal.

TABLE 2

Experimental hyperglycaemia tests in the rat

|  | Serum glucose (mg/dl) | |
| --- | --- | --- |
| Treatment | Initial | After 21 days |
| Controls | 456.8 ± 26 | 505.5 ± 31 |
| Acetyl L-carnitine | 509.5 ± 28 | 405.9 ± 25 |
| Carnitine mixture | 490.2 ± 32 | 410.5 ± 35 |
| α-lipoic acid | 502.8 ± 36 | 360.4 ± 30 |

TABLE 2-continued

Experimental hyperglycaemia tests in the rat

|  | Serum glucose (mg/dl) | |
| --- | --- | --- |
| Treatment | Initial | After 21 days |
| Acetyl L-carnitine + α-lipoic acid | 489.6 ± 40 | 145.5 ± 21 |
| Carnitine mixture + α-lipoic acid | 505.5 ± 39 | 170.5 ± 36 |

Acetyl L-carnitine = 200 mg/kg
Carnitine mixture = acetyl L-carnitine + propionyl L-carnitine + isovaleryl L-carnitine in a 1.1 ratio to one another
α-Lipoic acid = 50 mg/kg Test of Sorbitol Content in Ocular Lens and Sciatic Nerve in the Diabetic Rat One of the most frequent causes of lesions induced by diabetic hyperglycaemia and of the ocular or peripheral nervous diseases associated with it consists in the intracellular accumulation of sorbitol, with consequent reduction of osmotic capacity and cell integrity.

These tests were conducted in a group of rats in which diabetes was induced by means of the intravenous administration of 50 mg/kg of streptozotocin. One week after injection, serum glucose was tested and those rats were considered diabetic which presented serum glucose values above 450 mg/dl. These animals then received intraperitoneal injections, for eight consecutive days, of acetyl L-carnitine (100 mg/kg), or carnitine mixture (acetyl L-carnitine+propionyl L-carnitine+isovaleryl L-carnitine in a 1:1 weight ratio to one another) (100 mg/kg), or (x-lipoic acid (25 mg/kg), either alone or in various combinations.

After eight days of treatment, after suitable isolation, the sorbitol concentration present in both the sciatic nerve and the ocular lens of diabetic rats was measured before and after the treatment administered. The sorbitol concentration appeared to be decreased in all animals treated, but the most marked reduction was that detectable in the animals treated with the combination of α-lipoic acid and carnitines, and the lowest values were recorded in the group treated with the combination of acetyl L-carnitine and α-lipoic acid .

The results of these tests also show a surprising degree of synergistic potentiation activity between α-lipoic acid and carnitine p.

TABLE 3

Sorbitol content in ocular lens and sciatic nerve in the diabetic rat

|  | Sorbitol (nmol/mg) | |
| --- | --- | --- |
| Treatment | Lens | Sciatic nerve |
| Controls | 0.44 ± 0.06 | 0.078 ± 0.008 |
| Diabetics | 40.2 ± 3.9 | 1.85 ± 0.21 |
| Acetyl L-carnitine | 32.7 ± 2.5 | 1.15 ± 0.11 |
| Carnitine mixture | 30.5 ± 2.9 | 1.05 ± 0.09 |
| α-lipoic acid | 30.8 ± 3.2 | 1.08 ± 0.10 |
| Acetyl L-carnitine + α-lipoic acid | 14.7 ± 2.8 | 0.55 ± 0.08 |
| Carnitine mixture + α-lipoic acid | 16.4 ± 1.9 | 0.65 ± 0.07 |

Tests of Survival and Growth of Nerve Cells Treated with IGFc-I Carnitines and α-lipoic Acid In view of the important role that insulin-like growth factor (IGF-I) plays in protecting the functional integrity of nerve cells, particularly against toxic lesion s such as those presenting in the course of diabetic diseases, we considered whether the activity of IGF-I favouring the growth and survival of brain cells was facilitated by the presence in the culture medium of carnitines, or α-lipoic acid, or of these products in combination. To this end, brain cells of Wistar rats were isolated according to the method described by Thanguipon (Thanguipon W., *Dev. Brain Res.*, 11, 177, 1983) and were distributed on plates with a density of $3 \times 10^5/cm^2$. To the culture medium was added cytosine arabino-furanoside (10 mM) to prevent the replication of non-neuronal cells. After eight days, the cells were washed and maintained in a culture in which the serum was replaced with BME (Basal Eagles Medium, Life Technologies, Gaithersburg, Md.) containing a 5 mM KCl concentration. The test products were added directly to the serum thus prepared: IGF-I corresponding to 25 ng/ml acetyl L-carnitine (100 ng/ml) or carnitine mixture (100 ng/ml) or α-lipoic acid, either alone or in combination.

Cell survival and growth in culture were observed 24 hours after addition of the substances to the medium, on 35 mm disks in contact with 10 ng/ml of fluorescein acetate according to the technique described by Jones (Jones K. H., *J. Histochem. Cytochem.*, 33, 77, 1985). The cell count was done with a fluorescence microscope. The results of this test indicate that the growth-promoting effect of IGF-I on isolated brain cells is significantly potentiated by the presence of carnitines and α-lipoic acid, which alone do not give rise to significant changes, and that the greatest growth-potentiating effect is that induced when carnitines, and particularly acetyl L-carnitine, are combined with α-lipoic acid.

TABLE 4

Tests of potentiation of IGF-1 enhancement of isolated brain cell growth by acetyl L-carnitine, carnitine mixture, and α-lipoic acid

| Treatment | Cell growth (% vs controls) |
| --- | --- |
| IGF-I | 45 ± 2.8 |
| Acetyl L-carnitine | 5 ± 0.51 |
| Carnitine mixture | 9 ± 0.91 |
| α-lipoic acid | 5 ± 0.39 |
| IGF-I + acetyl L-carnitine | 65 ± 5.8 |
| IGF-I + carnitine mixture | 60 ± 3.5 |
| IGF-I + α-lipoic acid | 70 ± 6.1 |
| IGF-I + acetyl L-carnitine + α-lipoic acid | 98 ± 7.3 |
| IGF-I + carnitine mixture + α-lipoic acid | 90 ± 6.9 |

Sciatic Nerve Regeneration Tests in Diabetic Rats

Rats with induced diabetes whose sciatic nerve has been cut present inferior regenerative activity to that of normal rats.

These tests were conducted to investigate whether regeneration of the sciatic nerve in diabetic rats may be accelerated by treatment with acetyl L-carnitine, carnitine mixture, or α-lipoic acid, or combinations of these products. The technique used in these tests is the one described by Fernandez (Fernandez E., *Int. J. Clin. Pharmacol. Res.*, 10, 85, 1990).

Diabetes (serum glucose above 450 mg/dl) was induced in a group of rats by subcutaneous injection of 100 mg/kg of alloxan. Acetyl L-carnitine, carnitine mixture and α-lipoic acid were administered with the diet in such a way that the daily intake was 200 mg/kg of acetyl L-carnitine, 200 mg/kg of carnitine mixture (acetyl L-carnitine+propionyl L-carnitine+isovaleryl L-carnitine in a 1:1 weight ratio to one another) and 50 mg/kg of α-lipoic acid. The compounds were administered a week before cutting the sciatic nerve and for thirty days after cutting.

The sciatic nerve was cut under anaesthesia and after exposing 1 cm of it at the level of the sciatic foramen. The border of the lesion was marked with an epineural suture. Thirty days after cutting the nerve, the tissue of the tibial nerve, one of the main divisions of the sciatic nerve, was examined, after sacrificing the animals. Four cross-sections of the tibial nerve measuring approximately 4 mm in length were thus subjected to morphological and morphometric examination by means of a semiautomatic image analyser (Zeiss Videoplan Image Analyser).

The number of regenerating axons and their density per 100 nm$^2$ were counted, as well as the degenerate elements. It thus proved possible to detect the diabetes-induced degeneration of the tibial nerve elements, which was corrected almost to the extent of restoring normal values by treatment with acetyl L-carnitine, carnitine mixture, and α-lipoic acid.

The most evident results in terms of prevention of diabetic damage to nerve regeneration were those obtained with the administration of acetyl L-carnitine or carnitine mixture in combination with α-lipoic acid, thus demonstrating, in this test, too, a marked and unexpected synergism on the part of the combination according to the invention.

TABLE 5

Number and density of tibial nerve degenerate elements after cutting the sciatic nerve in diabetic rats

| Treatment | Number | Density (per 100 nm$^2$) |
| --- | --- | --- |
| Controls | 965 ± 141 | 0.31 ± 0.04 |
| Acetyl L-carnitine | 560 ± 61 | 0.16 ± 0.02 |
| Carnitine mixture | 520 ± 55 | 0.14 ± 0.02 |
| α-lipoic acid | 590 ± 0.70 | 0.20 ± 0.04 |
| Acetyl L-carnitine + α-lipoic acid | 340 ± 0.41 | 0.10 ± 0.01 |
| Carnitine mixture + α-lipoic acid | 360 ± 0.55 | 0.11 ± 0.02 |

Neuromuscular Conduction Tests

One of the most evident abnormalities in peripheral neuropathies and particularly in diabetic neuropathy is the slowing down of neuromuscular conduction which is reflected in changes in motor activity.

In these tests, we induced experimental diabetes in rats by intravenously injecting the experimental animals (rats with a mean weight of 300 g) with 50 mg/kg of streptozotocin. In the animals with induced diabetes (serum glucose above 450 mg/dl) the neuromuscular conduction velocity (NMCN7) was measured. To this end, the sciatic nerve was isolated (2 cm length) and the soleus muscle was separated from the gastrocnemius and its distal tendon cut and connected up to an isometric transducer which recorded the muscular contraction force (MCF). The muscle was stimulated via the sciatic nerve by means of two electrodes inserted at a distance of 10 mm from the nerve and connected up to a stimulator.

A bipolar electrode was placed in the distal end of the muscle for displaying the electromyogram via an oscilloscope.

The NMCV was measured in m/sec, dividing the distance between the stimulation electrodes by the mean difference in latency between the start of the ECG potentials evoked in the two sites. The MCF was expressed in mm.

TABLE 6

Neuromuscular conduction tests in the diabetic rat (after 4 weeks)

| Treatment | NMCV (m/sec) | MCF (mm) |
| --- | --- | --- |
| Controls | 42.2 ± 2.4 | 49.3 ± 3.1 |
| Diabetics | 34.5 ± 2.1 | 34.6 ± 2.9 |
| Diabetics + acetyl L-carnitine | 38.5 ± 1.9 | 40.6 ± 3.4 |
| Diabetics + carnitine mixture | 39.9 ± 2.1 | 41.2 ± 2.7 |
| Diabetics + α-lipoic acid | 40.1 ± 1.5 | 41.9 ± 3.3 |
| Diabetics + acetyl L-carnitine + α-lipoic acid | 43.4 ± 2.4 | 48.9 ± 3.9 |
| Diabetics + carnitine mixture + α-lipoic acid | 42.0 ± 3.1 | 47.5 ± 4.1 |

Motor Co-ordination Abnormality Test

These tests were conducted in "wobbler mice", that is to say animals that present an unsteady, staggering gait, an abnormal position of the paws and a reduced speed of movement. These abnormalities are related to progressive atrophy of the motoneurons and musculo-cutaneous nerve fibres, particularly as affecting the anterior limbs. The tests were conducted according to the procedure proposed by Mitsumoto (Mitsumoto H., *Annal. Neurol.*, 36, 14, 1994). After diagnosis the wobbler mice were treated orally for twenty days consecutively with acetyl L-carnitine (200 mg/kg), or with carnitine mixture (200 mg/kg), or with α-lipoic acid (50 mg/kg), or with these products in various combinations. The examination was performed by evaluating, in the treated animals versus controls, the time that each animal holds on to the edge of an inclined platform (holding time) and also the time it takes to run a distance of 10 cm (running time).

The results of these tests indicate that the treatment of these animals with acetyl L-carnitine, carnitine mixture and α-lipoic acid improves both holding time and running time as compared to controls, but also that the best effects are obtained with the administration of these products in combination and in particular by the combination of acetyl L-carnitine and α-lipoic acid. In these tests, too, there is a marked, unexpected synergistic potentiating effect of carnitines and α-lipoic acid.

TABLE 7

Tests of percentage increase in running time

| | |
| --- | --- |
| Controls | 55 ± 4.5 |
| Acetyl L-carnitine | 35 ± 3.2 |
| Carnitine mixture | 38 ± 4.1 |
| α-lipoic acid | 40 ± 3.9 |
| Acetyl L-carnitine + α-lipoic acid | 20 ± 1.9 |
| Carnitine mixture + α-lipoic acid | 26 ± 2.1 |

TABLE 8

Tests of percentage increase in holding time

| | |
| --- | --- |
| Controls | 70 ± 5.5 |
| Acetyl L-carnitine | 55 ± 4.6 |
| Carnitine mixture | 60 ± 3.8 |
| α-lipoic acid | 50 ± 5.9 |
| Acetyl L-carnitine + α-lipoic acid | 25 ± 3.2 |
| Carnitine mixture + α-lipoic acid | 30 ± 2.8 |

Tests of Cisplatin-induced Sensory Neuronal Lesions

The prolonged administration of cisplatin to experimental animals is capable of causing lesions at the level of the sensory neurons and of causing marked abnormalities of propioceptive perception.

In these tests, we evaluated the protective effect exerted by the administration, for seven consecutive days, of 300 mg/kg of acetyl L-carnitine orally, or 300 mg/kg of carnitine mixture (acetyl L-carnitine+propionyl L-carnitine+ isovaleryl L-carnitine in a 1:1 weight ratio to one another), or of 50 mg/kg of α-lipoic acid, or of these products in various combinations on the toxicity induced by the subcutaneous injection of 10 mg/kg of cisplatin for seven days consecutively.

The proprioceptive sensory perception abnormalities induced by cisplatin in the mouse were evaluated by means of the rotarod test (Apfel, S. C., *Ann. Neurol.*, 29, 89, 1991).

The results obtained in these tests demonstrate that, whereas cisplatin causes a substantial reduction in equilibrium time in cisplatin-treated animals as compared to control animals and reductions of the same order in the animals treated with acetyl L-carnitine or α-lipoic acid alone, the group of animals treated with the combination of acetyl L-carnitine and α-lipoic acid, on the other hand, show an equilibrium capability practically identical to that of the animals not subjected to cisplatin intoxication. In these tests, too, there is a marked, synergistic effect of carnitines and α-lipoic acid.

TABLE 9

Tests of neurosensory abnormalities induced by cisplatin (rotarod test)

| Cisplatin | Treatment | Equilibrium time (in seconds) |
| --- | --- | --- |
| — | Controls | 14.8 ± 1.4 |
| Cisplatin | — | 8.4 ± 0.8 |
| Cisplatin | acetyl L-carnitine | 9.5 ± 0.6 |
| Cisplatin | carnitine mixture | 8.9 ± 0.6 |
| Cisplatin | α-Lipoic acid | 9.9 ± 0.8 |
| Cisplatin | acetyl L-carnitine + α-lipoic acid | 14.4 ± 1.8 |
| Cisplatin | carnitine mixture + α-lipoic acid | 13.8 ± 2.1 |

The tests performed to evaluate the activity that the new composition is capable of exerting fully justify the innovative nature of the invention itself and demonstrate above all the unexpected and surprising synergistic effect which its components are capable of inducing when used in combination.

On the basis of the synergistic interaction of its components, the composition according to the invention described herein is suitable for preventing toxic and metabolic damage which gives rise to neuronal lesions of an acute or chronic nature. In particular, it can be used in the treatment of toxic neuropathies, especially diabetic peripheral neuropathies.

In view of its antioxidant capability, this composition is also indicated in the prevention or treatment of abnormalities of toxic or anoxic origin related to the release of free radicals in the brain, liver, heart or other organs and tissues.

Furthermore, in view of the ability of the composition to promote the action of IGF-I, pathological abnormalities related to ageing, such as neuro- degenerative disorders, may also obtain satisfactory benefit from its use.

Illustrative, non-limiting examples of formulations according to the invention are reported hereinbelow.

| | | | |
|---|---|---|---|
| 1) | Acetyl L-carnitine | mg | 500 |
| | α-lipoic acid | mg | 50 |
| 2) | Carnitine mixture | mg | 500 |
| | (acetyl L-carnitine, propionyl L-carnitine, isovaleryl L-carnitine in identical weight amounts) | | |
| | α-lipoic acid | mg | 50 |
| 3) | Acetyl L-carnitine | mg | 250 |
| | α-lipoic acid | mg | 25 |
| 4) | Carnitine mixture | mg | 250 |
| | (acetyl L-carnitine, propionyl L-carnitine, isovaleryl L-carnitine in identical weight amounts) | | |
| | α-lipoic acid | mg | 25 |
| 5) | Acetyl L-carnitine | mg | 1 |
| | α-lipoic acid | mg | 100 |
| 6) | Acetyl L-carnitine | mg | 250 |
| | α-lipoic acid | mg | 25 |
| | Selenium methionine | μg | 50 |
| | Zinc glycinate | mg | 10 |
| | Magnesium stereate | mg | 20 |
| | Taurine | mg | 50 |
| | Vit. E | mg | 10 |
| | $CoQ_{10}$ | mg | 10 |
| | β-carotene | mg | 10 |
| | Vit. C | mg | 30 |

What is meant by pharmacologically acceptable salt of L-carnitine or alkanoyl L-carnitine is any salt of these active ingredients with an acid that does not give rise to unwanted toxic or side effects. These acids are well known to pharmacy experts.

Non-limiting examples of suitable salts are the following: chloride; bromide; iodide; aspartate, acid aspartate; citrate, acid citrate; tartrate; phosphate, acid phosphate; fumarate; acid fumarate; glycerophosphate; glucose phosphate; lactate; maleate, acid maleate; orotate; oxalate, acid oxalate; sulphate, acid sulphate, trichloroacetate, trifluoroacetate and methanesulphonate.

A list of FDA-approved pharmacologically acceptable salts is given in Int. J. of Pharm. 33, (1986), 201—217; this latter publication is incorporated herein by reference.

The composition according to the invention may also comprise vitamins, coenzymes, minerals substances and antioxidants.

Appropriate excipients to be used to prepare the compositions having regards to the specific route of administration, will be apparent to the pharmacy and food industry experts.

What is claimed is:

1. A combination composition which comprises:
   (a) acetyl L-carnitine or a pharmacologically acceptable salt thereof; and
   (b) α-lipoic acid in a synergistically effective weight ratio.

2. The composition of claim 1, wherein ingredient (a) further comprises a carnitine selected from the group consisting of L-carnitine, propionyl L-carnitine, valeryl L-carnitine, isovaleryl L-carnitine and their phramacologially acceptable salts or mixtures thereof.

3. The composition of claim 1 or 2 wherein the weight ratio (a):(b) is from 100:1 to 1:10.

4. The composition of claim 1 wherein a pharmacologically acceptable salt of acetyl L-carnitine is selected from the group consisting of chloride, bromide, iodide, aspartate, acid aspartate, citrate, acid citrate, tartrate, phosphate, acid phosphate, fumarate, acid fumarate, glycerophosphate, glucose phosphate, lactate, maleate, acid maleate, orotate, acid oxalate, sulphate, acid sulphate, trichloroacetate, trifluoroacetate and methane sulfonate.

5. The composition of claim 2 wherein the carnitine selected is the pharmacologically acceptable salt of L-carnitine or alkanoyl L-carnitine selected from the group consisting of chloride, bromide, iodide, aspartate, acid aspartate, citrate, acid citrate, tartrate, phosphate, acid phosphate, fumarate, acid fumarate, glycerophosphate, glucose phosphate, lactate, maleate, acid maleate, orotate, acid oxalate, sulphate, acid sulphate, trichloroacetate, trifluoroacetate and methane sulphonate.

6. The composition of claim 1 or 2 which further comprises vitamins, coenzymes, mineral substances or antioxidants.

7. The composition of claim 1 or 2 in an orally administrable form as a dietary supplement.

8. The composition of claim 1 or 2 in an orally, parenterally, rectally or transdermally administrable form as a medicament.

9. The composition of claim 7 in solid, semi-solid or liquid form.

10. The composition of claim 9 in the form of tablets, lozenges, pills, capsules, granulates or syrups.

11. The composition of claim 10 in the form of tablets, lozenges, pills, capsules, granulates, syrups, injection or drops.

12. A method of preventing tissue damage brought about by the presence of free radicals due to environmental pollution; for preventing brain or myocardial lesions induced by free radicals following cerebral or myocardial ischaemia and attendant reperfusion; for preventing diabetic or toxic neuropathies; or metabolic disorders in glucose utilization, said method comprising administering to a subject in need of same a composition which in combination comprises:
   (a) acetyl L-carnitine or a pharmacologically acceptable salt thereof and optionally also a carnitine selected from the group consisting of L-carnitine, propionyl L-carnitine, valeryl L-carnitine, isovaleryl L-carnitine or their pharmacologically acceptable salts or mixtures thereof and
   (b) α-lipoic acid.

13. A method of treating a disease brought about by the presence of free radicals due to environmental pollution; brain or myocardial lesions induced by free radicals following cerebral or myocardial ischaemia and attendant reperfusion; atherosclerosis lesions and tissue proliferative processes; diabetic or toxic neuropathies; and of metabolic disorders in glucose utilization, said method comprising administering to a subject in need of same a composition which in combination comprises:
   (a) acetyl L-carnitine or a pharmacologically acceptable salt thereof and optionally also a carnitine selected from the group consisting of L-carnitine, propionyl L-carnitine, valeryl L-carnitine, isovaleryl L-carnitine or their pharmacologically acceptable salts or mixtures thereof and
   (b) α-lipoic acid.

14. The method of claim 12 wherein the weight ratio (a):(b) is from 100:1 to 1:10.

15. The method of claim 13 wherein the weight ratio (a):(b) is from 100:1 to 1:10.

* * * * *